(12) United States Patent
Ghare

(10) Patent No.: US 8,278,478 B2
(45) Date of Patent: Oct. 2, 2012

(54) PROCESS FOR THE SYNTHESIS OF HYDROCHLORIDE SALT OF N-FATTY ACYLSUBSTITUTED AMINO ACID ETHYL ESTERS

(76) Inventor: Vishwas Sadhu Ghare, Maharashtra (IN)

( * ) Notice: Subject to any disclaimer, the term of this patent is extended or adjusted under 35 U.S.C. 154(b) by 212 days.

(21) Appl. No.: 12/888,583

(22) Filed: Sep. 23, 2010

(65) Prior Publication Data

US 2011/0077423 A1 Mar. 31, 2011

Related U.S. Application Data

(60) Provisional application No. 61/247,272, filed on Sep. 30, 2009.

(51) Int. Cl.
*C07C 229/00* (2006.01)
(52) U.S. Cl. .......................................................... 560/169
(58) Field of Classification Search ................... 560/169
See application file for complete search history.

(56) References Cited

U.S. PATENT DOCUMENTS 7,087,769 B1 8/2006 Contijoch Manent et al.

FOREIGN PATENT DOCUMENTS

EP 0749960 A1 12/1996

*Primary Examiner* — Deborah D Carr
(74) *Attorney, Agent, or Firm* — Robert P. Michal; Lucas & Mercanti, LLP

(57) ABSTRACT

The present invention relates to a process for preparing hydrochloride salt of N-fatty acyl substituted amino acid ethyl ester. Said process includes the steps of: dissolving L-arginine ethyl ester dihydrochloride in distilled water with continuous agitation for a period of about 10 to about 20 minutes to obtain a clear solution; lowering the temperature of the clear solution to about 5° C. to about 10° C. to obtain a cooled solution; adjusting the pH of the cooled solution in the range of about 7 to about 8 by adding sodium hydroxide solution; adding at least one organic solvent to the clear solution with continuous agitation to obtain an intermediate mixture; condensing the intermediate mixture by simultaneously adding an acid halide and 20% sodium hydroxide solution at a temperature of about 7° C. to about 9° C. and at a pH in the range of about 7.2 to about 7.5 for about 2 hours to obtain a mixture; raising the temperature of the mixture to about 18 to about 20° C. followed by addition of sodium hydroxide to adjust the pH of the mixture to about 7.3; warming the mixture at a temperature of about 25 to about 30° C. to obtain a resultant mixture containing organic phase and aqueous phase; separating the organic phase and aqueous phase of the resultant mixture by settling the mixture; and distilling the organic phase under vacuum at a temperature of about 70° C. to about 75° C. to obtain a hydrochloride salt of ethyl lauroyl arginate.

7 Claims, No Drawings

PROCESS FOR THE SYNTHESIS OF HYDROCHLORIDE SALT OF N-FATTY ACYLSUBSTITUTED AMINO ACID ETHYL ESTERS

CROSS-REFERENCE TO RELATED APPLICATIONS

This application claims priority under 35 U.S.C. §119(e) to U.S. Provisional Patent Application No. 61/247,272, filed Sep. 30, 2009, entitled "A PROCESS FOR THE SYNTHESIS OF HYDROCHLORIDE SALT OF N-FATTY ACYL-SUBSTITUTED AMINO ACID ETHYL ESTERS", the disclosure of which is incorporated by reference herein in its entirety.

FIELD OF THE INVENTION

The present invention relates to a process for synthesis of hydrochloride salt of N-fatty acylsubstituted amino acid ethyl esters.

BACKGROUND OF THE INVENTION

Ethyl lauroyl arginate hydrochloride (ELA) is derived from naturally occurring substances, L-arginine and lauric acid. It has cationic surfactant properties. It also has antimicrobial activity against bacteria, algae and fungi. ELA acts by modifying the permeability of cell membranes of living organisms. It is mainly known to be effective against the gram positive bacteria and gram negative bacteria. It is envisaged that it would be used as a multi functional component in the formulation of cosmetic products. The active ingredient of ethyl lauroyl arginate is the hydrochloride salt of an N-fatty acyl-substituted amino acid ethyl ester, ethyl-Nα-lauroyl-L-arginate HCl.

Ethyl lauroyl arginate is a white powder and its solubility in water at 20° C. is greater than 247 g/kg.

Structure of Ethyl N-lauroyl-L-arginate HCl

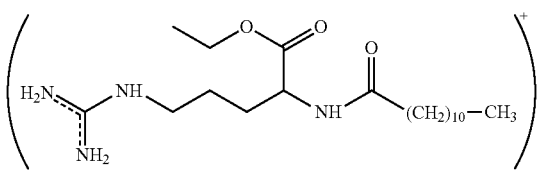

Ethyl lauroyl arginate hydrochloride and its hydrolysis products have been sufficiently characterized to assure safe human consumption. Because of its antimicrobial properties, cationic surfactant activity and due to its non-toxicity it is useful as surfactant, antimicrobial and anti-static agent in cosmetic and toiletry formulations such as soaps, oral care products, deodorants, anti-dandruff shampoos. It is also useful as a preservative in the food industry.

Methods of synthesis of ethyl lauroyl arginate hydrochloride have been reported in several patents/patent applications.

Following patents/applications disclose methods of synthesis of ethyl lauroyl arginate hydrochloride Patent No. ES512643 discloses a process for synthesis of ethyl lauroyl arginate hydrochloride in two steps. The first step is the esterification of basic amino acid with alcohol, using thionyl chloride as a catalyst to give esterified amino acid and the second step is the condensation of an esterified amino acid derivative with a fatty acid as a free acid in the presence of coupling reagent such as dicyclohexylcarbodiimide (DCC). Furthermore, the first step of esterification involves heating for about 16 hours.

In another, Patent EP0749960, a two-step process for preparation of ethyl lauroyl arginate hydrochloride is disclosed. The first step is the esterification of amino acid with alcohol in presence of thionyl chloride as a catalyst. Step one is differing from step one disclosed in ES512643 by providing in the first step a dispersion of the basic type amino acid in alcohol and adding catalyst like thionyl chloride to this dispersion in drop-wise manner. A further difference is that the second step i.e. the condensation of an esterified amino acid derivative is carried out with fatty acid halide instead of fatty acid Furthermore, the second step of condensation of esterified amino acid is performed in aqueous alkaline medium at pH about 8-10.

Further, U.S. Pat. No. 7,087,769 discloses a process for the preparation of cationic surfactants derived from the condensation of fatty acid chlorides with esterified amino acids in an aqueous medium in the pH range of 6 and 6.9.

Still further, Indian Patent application No. 2616/MUM/2008 discloses methods of synthesizing ethyl lauroyl arginate.

The yield obtained in these prior art processes is low. Further, the aforesaid processes do not provide a comparatively pure product. Accordingly, it is desirable to develop a single pot process for the synthesis of a hydrochloride salt of ethyl lauroyl arginate on the commercial scale which can provide a better control of parameters like temperature and pH during the reaction process as well provides better quality and quantity product with ease of isolation.

OBJECTS OF THE INVENTION

It is an object of the present invention to provide a process for the synthesis of hydrochloride salt of ethyl lauroyl arginate with improved yield and purity.

It is another object of the present invention to provide a process for the synthesis of hydrochloride salt of ethyl lauroyl arginate, which provides better temperature and pH control during the reaction.

It is still another object of the present invention to provide a process for the synthesis of hydrochloride salt of ethyl lauroyl arginate, which provides ease of isolation of the product.

It is yet another object of the present invention to provide a process for the synthesis of hydrochloride salt of ethyl lauroyl arginate, which is simple, easy, efficient and cost effective.

It is a further object of the present invention to provide a process for the synthesis of hydrochloride salt of ethyl lauroyl arginate which is safe.

SUMMARY OF THE INVENTION

In accordance with the present invention there is provided a process for preparing hydrochloride salt of ethyl lauroyl arginate; said process comprising the following steps:
  a. dissolving L-arginine ethyl ester dihydrochloride in distilled water with continuous agitation for a period of about 10 to about 20 minutes to obtain a clear solution;
  b. lowering the temperature of the clear solution to about 5° C. to about 10° C. to obtain a cooled solution;
  c. adjusting the pH of the cooled solution in the range of about 7 to about 8 by adding sodium hydroxide solution;
  d. adding at least one organic solvent to the clear solution with continuous agitation to obtain an intermediate mixture;

e. condensing the intermediate mixture by simultaneously adding an acid halide and 20% sodium hydroxide solution at a temperature of about 7° C. to about 9° C. and at a pH in the range of about 7.2 to about 7.5 for about 2 hours to obtain a mixture;
f. raising the temperature of the mixture to about 18 to about 20° C. followed by addition of sodium hydroxide to adjust the pH of the mixture to about 7.3;
g. warming the mixture at a temperature of about 25 to about 30° C. to obtain a resultant mixture containing organic phase and aqueous phase;
h. separating the organic phase and aqueous phase of the resultant mixture by settling the mixture; and
i. distilling the organic phase under vacuum at a temperature of about 70° C. to about 75° C. to obtain a hydrochloride salt of ethyl lauroyl arginate.

Typically, the organic solvent is at least one selected from the group of solvents consisting of ethyl acetate, methyl acetate, butyl acetate and ethyl formate.

Preferably, the organic solvent used is ethyl acetate.

Typically, the acid halide is at least one selected from the group consisting of fatty acid halides and hydroxy acid halides.

Typically, the acid halide is fatty acid chloride.

Typically, the fatty acid chloride is at least one selected from the group consisting of chlorides of lauric acid, caprylic acid, capric acid, myristic acid and palmitic acid.

Preferably, the fatty acid chloride is lauroyl chloride.

DESCRIPTION OF THE INVENTION

In accordance with the present invention there is provided a process for preparing hydrochloride salt of ethyl lauroyl arginate; said process comprising the following steps: In first step, L-arginine ethyl ester dihydrochloride is dissolved in distilled water with continuous agitation for a period of about 10 to about 20 minutes to obtain a clear solution followed by lowering the temperature of the clear solution to about 5° C. to about 10° C. to obtain a cooled solution.

In next step, the pH of the obtained cooled solution is adjusted in the range of about 7 to about 8 by adding sodium hydroxide solution. To this solution at least one organic solvent is added with continuous agitation to obtain an intermediate mixture.

Typically, the organic solvent is at least one selected from the group of solvents consisting of ethyl acetate, methyl acetate, butyl acetate and ethyl formate.

Preferably, the organic solvent used is ethyl acetate.

The obtained intermediate mixture is condensed by simultaneously adding an acid halide and 20% sodium hydroxide solution at a temperature of about 7° C. to about 9° C. and at a pH in the range of about 7.2 to about 7.5 for about 2 hours to obtain a mixture.

Typically, the acid halide is at least one selected from the group consisting of fatty acid halides and hydroxy acid halides.

Typically, the acid halide is fatty acid chloride.

Typically, the fatty acid chloride is at least one selected from the group consisting of chlorides of lauric acid, caprylic acid, capric acid, myristic acid and palmitic acid.

In accordance with the preferred embodiment of the present invention the fatty acid chloride employed in the reaction is lauroyl chloride.

The temperature of the mixture is then raised to about 18 to about 20° C. followed by addition of sodium hydroxide to adjust the pH of the mixture to about 7.3.

Further, the temperature of the mixture is adjusted to about 25 to about 30° C. to obtain a resultant mixture containing organic phase and aqueous phase. The organic phase and aqueous phase of the resultant mixture are then separated by settling the mixture.

In the final step, the organic phase is distilled under vacuum at a temperature of about 70° C. to about 75° C. to obtain a hydrochloride salt of ethyl lauroyl arginate.

In accordance with the present invention, a process for the synthesis of ethyl lauroyl arginate hydrochloride will now be described with respect to the following example which does not limit the invention in any way and only exemplifies the invention.

EXAMPLE 47.1 gm of L-arginine ethyl ester dihydrochloride was transferred to a flask containing 250 gm of water and was stirred for 10 minutes to obtain a clear solution. This solution was cooled to 8° C. followed by addition of 20% sodium hydroxide solution to adjust the pH to 7.5. To this solution 250 gm of ethyl acetate was added with agitation. Further, lauroyl chloride and 20% sodium hydroxide solution were added simultaneously to above solution at a temperature of about 8° C. and at pH 7.5 for about 2 hours to obtain the mixture. Then the cooling was removed and the temperature of the mixture was raised to 19° C. and the pH was adjusted to 7.3 by adding sodium hydroxide solution. The mixture was then warmed to a temperature of about 25° C. to obtain the mixture containing two phases. The upper phase containing the product was separated and distilled under vacuum (50 mmHg) at a temperature of about 75° C. to obtain the white crystals of hydrochloride salts of ethyl lauroyl arginate.

(% Yield—98% w/w, HPLC purity—98.4%)

Technical Advancement

The process in accordance with the present invention is a single pot reaction which involves unique step of adding solvent during the coupling step of Schotten Baumann reaction. Further, the method disclosed in the present invention provides better temperature and pH control during the synthesis of hydrochloride salt of ethyl lauroyl arginate. Still further, the method also provides better yield and ease of isolation of the product as the byproducts such as salts get dissolved in water and ethyl lauroyl arginate is extracted selectively.

While considerable emphasis has been placed herein on the specific ingredients of the preferred processes, it will be appreciated that many additional ingredients can be added and that many changes can be made in the preferred processes without departing from the principles of the invention. These and other changes in the preferred processes of the invention will be apparent to those skilled in the art from the disclosure herein, whereby it is to be distinctly understood that the foregoing descriptive matter is to be interpreted merely as illustrative of the invention and not as a limitation.

The invention claimed is:
1. A process for preparing hydrochloride salt of ethyl lauroyl arginate; said process comprising the following steps:
   a. dissolving L-arginine ethyl ester dihydrochloride in distilled water with continuous agitation for a period of about 10 to about 20 minutes to obtain a clear solution;
   b. lowering the temperature of the clear solution to about 5° C. to about 10° C. to obtain a cooled solution;
   c. adjusting the pH of the cooled solution in the range of about 7 to about 8 by adding sodium hydroxide solution;

d. adding at least one organic solvent to the clear solution with continuous agitation to obtain an intermediate mixture;
e. condensing the intermediate mixture by simultaneously adding an acid halide and 20% sodium hydroxide solution at a temperature of about 7° C. to about 9° C. and at a pH in the range of about 7.2 to about 7.5 for about 2 hours to obtain a mixture;
f. raising the temperature of the mixture to about 18 to about 20° C. followed by addition of sodium hydroxide to adjust the pH of the mixture to about 7.3;
g. warming the mixture at a temperature of about 25 to about 30° C. to obtain a resultant mixture containing organic phase and aqueous phase;
h. separating the organic phase and aqueous phase of the resultant mixture by settling the mixture; and
i. distilling the organic phase under vacuum at a temperature of about 70° C. to about 75° C. to obtain a hydrochloride salt of ethyl lauroyl arginate.

2. The process as claimed in claim 1, wherein the acid halide is at least one selected from the group consisting of fatty acid halides and hydroxy acid halides.

3. The process as claimed in claim 1, wherein the acid halide is fatty acid chloride.

4. The process as claimed in claim 1, wherein the acid halide is at least one selected from the group consisting of chlorides of lauric acid, caprylic acid, capric acid, myristic acid and palmitic acid.

5. The process as claimed in claim 1, wherein the acid halide is lauroyl chloride.

6. The process as claimed in claim 1, wherein the organic solvent is at least one selected from the group of solvents consisting of ethyl acetate, methyl acetate, butyl acetate and ethyl formate.

7. The process as claimed in claim 1, wherein the organic solvent is ethyl acetate.

* * * * *